United States Patent [19]
Cumbo et al.

[11] 3,963,755
[45] June 15, 1976

[54] MIXTURE OF 2(2'-PROPANAL)-5-METHYL-1,3-DIOXANE AND 2(3'-PROPANAL)-5-METHYL-1,3-DIOXANE

[75] Inventors: Charles C. Cumbo, Wilmington; Kamlesh K. Bhatia, Newark, both of Del.

[73] Assignee: E. I. Du Pont de Nemours and Company, Wilmington, Del.

[22] Filed: July 31, 1974

[21] Appl. No.: 493,742

[52] U.S. Cl. .......................... 260/340.7; 260/635 E
[51] Int. Cl.² ............... C07D 319/06; C07C 29/00
[58] Field of Search .................................. 260/340.7

[56] References Cited
UNITED STATES PATENTS 2,729,650   1/1956   Habeshaw et al................ 260/340.7

*Primary Examiner*—Anton H. Sutto

[57] ABSTRACT

2(2'-propanal)-5-methyl-1,3-dioxane and 2(3'-propanal)-5-methyl-1,3-dioxane are provided as new cyclic acetal-aldehydes which, when hydrolyzed and hydrogenated, provide high yields of a mixture of 1,4-butanediol and 2-methyl-1,3-propanediol.

1 Claim, No Drawings

MIXTURE OF 2(2'-PROPANAL)-5-METHYL-1,3-DIOXANE AND 2(3'-PROPANAL)-5-METHYL-1,3-DIOXANE

BACKGROUND OF THE INVENTION

This invention relates to unique cyclic acetalaldehydes which are particularly useful for preparing an advantageous diol product upon hydrolysis and hydrogenation.

There are many cyclic acetals which may be hydroformylated to produce acetal-aldehydes which can be hydrolyzed and hydrogenated to yield polyols, including diols. However, prior art cyclic acetal-aldehydes prepared from prior art cyclic acetals yield a polyol product containing three or more polyols upon hydrolysis and hydrogenation. Because the polyols in any such admixture have very similar physical properties, the separation of the mixture into its component parts is extremely difficult in many cases.

SUMMARY OF THE INVENTION

It has now been found that 2(2'-propanal)-5-methyl-1,3-dioxane and/or 2(3'-propanal)-5-methyl-1,3-dioxane (hereinafter referred to collectively as PMD) which are the hydroformylation reaction products of 2-vinyl-5-methyl-1,3-dioxane (VMD), are new cyclic acetal-aldehyde which possess novel properties and yield advantages which cannot be obtained from prior art cyclic acetal-aldehydes prepared from cyclic acetals other than VMD. In particular, the acetal-aldehydes of the invention, when hydrolyzed and hydrogenated, provide high yields of a unique mixture of only two polyols, 1,4-butanediol (BAD) and 2-methyl-1,3-propanediol (MPD), which can be easily and simply separated from one another. The acetal-aldehydes of this invention exist in the cis and trans forms.

DETAILED DESCRIPTION OF THE INVENTION

The new cyclic acetal-aldehydes (PMD) of this invention have the structure

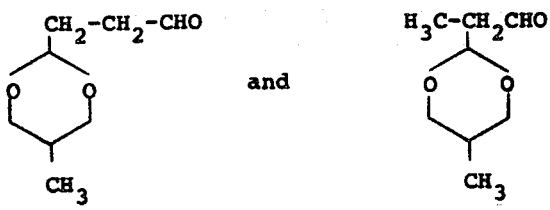

These cyclic acetal-aldehydes are prepared by reacting VMD with carbon monoxide and hydrogen under conventional hydroformylation reaction conditions. The 2-vinyl-5-methyl-1,3-dioxane (VMD) starting material can be prepared by reacting acrolein with 2-methyl-1,3-propanediol as described in U.S. Pat. Nos. 2,729,650 issued Jan. 3, 1956 to Habeshaw et al.; 2,840,615 issued June 24, 1968 to Stautzenberger; 2,987,524 issued June 6, 1961 to Fischer et al.; 2,566,559 issued Sept. 4, 1951 to Dolnick and Potash and the like. In a preferred process for preparing PMD, VMD is reacted in either a continuous or batch reaction with hydrogen and carbon monoxide at a molar ratio of $H_2:CO$ of 0.9:1 to 1.2:1, preferably 1:1. At ratios lower than 0.9:1, the reaction rates are too slow for commercial utility; at ratios higher than 1.2:1, hydrogenation of VMD occurs as an undesired side reaction. Best yields are obtained at the preferred ratio.

The preferred hydroformylation reaction is carried out in the presence of a rhodium carbonyl complex catalyst at a molar ratio to VMD of $0.5 \times 10^{-3}:1 - 6.0 \times 10^{-3}:1$, preferably $1 \times 10^{-3}:1 - 2 \times 10^{-3}:1$. At the preferred ratios, optimum yields and reaction rates result. The rhodium complex catalyst forms in situ when rhodium in the form of $Rh_6(CO)_{16}$ is added to the hydroformylation reaction mixture containing the ligand described below. The same rhodium carbonyl complex with a trialkyl phosphite may also be prepared first and then added to the reaction mixture.

The phosphite ligand used in the hydroformylation reaction has the formula

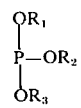

wherein $R_1$, $R_2$ and $R_3$ are the same or different alkyl groups having 1 – 12 carbon atoms such as, for example, methyl, ethyl, propyl, octyl, pentyl, decyl, dodecyl and the like or phenyl. For ease of operation, it is preferred that $R_1$, $R_2$ and $R_3$ are the same. Most preferably, $R_1$, $R_2$ and $R_3$ are the same alkyl groups having 1 – 3 carbon atoms such as trimethyl phosphite, triethyl phosphite, tri-n-propyl phosphite and triisopropyl phosphite since these materials are low boiling and easily separated, purified and recycled into the system. However, higher boiling phosphites within the scope of the above formula may also be used including tri-n-butyl phosphite, triisooctyl phosphite, dimethyldodecyl phosphite, tridecyl phosphite, triphenyl phosphite, methylethylpropyl phosphite, dimethyl phenyl phosphite, methylpropyl phenyl phosphite as well as any other combination within the definition of the above formula and mixtures of any of them.

The phosphite ligand forms a complex with rhodium and carbon monoxide as described in U.S. Patent 3,527,809, and this complex catalyzes the hydroformylation reaction. An excess of the phosphite over that which is required to complex with the rhodium must be used in order to prevent isomerization of the double bond in the VMD and to maximize the yield of linear aldehyde produced in the reaction. The excess ligand is also necessary to insure the stability of the rhodium catalyst throughout the reaction. Generally, a molar ratio of phosphite ligand to rhodium of from 5:1 – 50:1 is employed. In order to obtain optimum reaction rates and produce a product which will favor the formation of butanediol upon hydrolysis and hydrogenation, it is preferred that a ligand:rhodium molar ratio of from 10:1 – 20:1 be employed.

The hydroformylation reaction may be carried out batchwise or continuously as desired in any suitable reactor including a simple low pressure reactor. For ease of operation, it is preferred that the reaction be carried out in a continuous stage reactor through which the acetal flows cocurrently to the flow direction of the carbon monoxide and hydrogen gas. The reactor pressure should be from about 75 – 150 psig, preferably 100 – 110 psig. The reactor temperature should be from about 85° – 115°C., preferably 100° – 110°C. and the residence time in the reactor should be from 0.5 – 5 hours, preferably 1 – 2 hours. At the preferred conditions, the highest yields and best reaction rates are obtained.

After product stream exits from the reactor, the ligand is stripped off in any suitable manner. When the preferred ligands of this invention are used, the reaction product is preferably fed into a ligand stripper column maintained at a pressure of 10 mm. and a temperature of 110°C. Excess ligand is removed and recycled to the reactor. The product stream is then fed to an aldehyde vaporizer column maintained at a pressure of about 8 mm. and a temperature of 120°C. PMD is distilled off to be used in the hydrolysis-hydrogenation reaction. In order to prevent decomposition of the PMD, the temperature in this step should not exceed 120°C. and the PMD residence time should be less than 5 minutes. The bottom stream from this separation step contains some high boiling by-products which are unavoidably formed as well as all of the rhodium catalyst. This stream is recycled to the reactor after removing a small portion, about one-eighth, of the stream as a purge stream to control the buildup of high boilers. While it has been disclosed that the presence of these high boiling constituents is advantageous in some cases such as, for example, disclosed in U.S. Pat. No. 3,527,809 issued to Pruett on Sept. 8, 1970, it has been found that an acceptable maximum concentration of high boilers in this invention is about 50 percent, preferably 25 percent.

PMD can be hydrolyzed and hydrogenated using any conventional procedure such as those described in U.S. Pat. Nos. 2,729,650; 2,888,492 issued May 26, 1959 to Fischer et al.; 2,721,223 issued Oct. 18, 1955 to Arundale and Mikeska and the like. In a preferred embodiment, water is mixed with the PMD and the mixture is fed into a hydrogenation reactor at a temperature of 30° – 130°C., a pressure of 100 – 5,000 psig and a water:aldehyde molar ratio of 1:1 – 20:1. The aldehyde functional group is reduced to the corresponding alcohol in the presence of a catalytic amount of any hydrogenation catalyst such as Raney nickel, for example. As the reaction is continued, the acetal ring is thought to split to yield BAD and MPD which can be separated from one another by conventional distillation techniques. The MPD can be used in the preparation of the acetal from which PMD is produced. The BAD can be refined for use as such, for example, as a cross-linking agent in preparing polyurethane polymers, or it can be heated in a cyclization column, for example, to produce tetrahydrofuran.

The invention is further illustrated but is not intended to be limited by the following examples in which all parts and percentages are by weight unless otherwise specified.

EXAMPLE 1

Into a 400 cc. lined glass autoclave equipped with a stirrer are charged, in an atmosphere of dry nitrogen, 15.4 g. (0.12 mole) of VMD, 0.025 g. (2.3 × 10⁻⁵ mole) of hexarhodium hexadecacarbonyl and 250 μl. of trimethyl phosphite. The molar ratio of trimethyl phosphite to rhodium is 14.3:1. The autoclave is then charged with a 1:1 molar ratio of carbon monoxide-hydrogen gas to a pressure of 95 psig. The contents are heated to 110°C. and the pressure is adjusted to 105 psig, and maintained throughout the reaction. After 55 minutes 96 percent of the theoretical amount of gas is absorbed by the reaction mixture. At the end of that time the autoclave is cooled and the excess gases are vented. The liquid contents are removed and analyzed by gas-liquid phase chromatography. Analysis of the product shows a 97 percent conversion of VMD to the following products at the mole percentages specified.

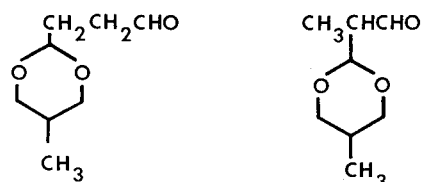

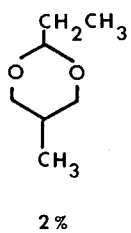

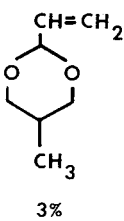

The aldehydes have a normal/iso ratio of 87/13.

36.4 g. of the aldehydes prepared above are mixed with 30 ml. of a 10 percent aqueous solution of acetic acid and hydrolyzed and hydrogenated at 100°C. and 1,000 psig of hydrogen using 3 g. of 10 percent palladium on charcoal. The reaction product is filtered and the water and acetic acid removed by distillation. Gas-liquid phase chromatographic analysis shows that only MPD (96 percent yield) and BAD (98 percent yield) are formed in the reaction.

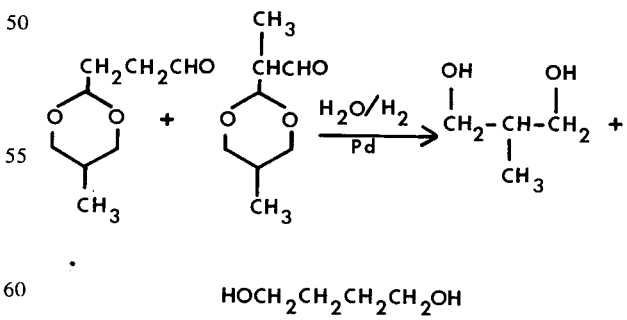

EXAMPLES 2–6

Example 1 is repeated except that 0.23 mole of cyclic acetal-aldehydes prepared from cyclic acetals other than VMD are used in the hydrolysis/hydrogenation reaction of Examples 3–6.

TABLE I

| Example | Cyclic Acetal | Acetal-Aldehydes (mole %) | | Hydrolysis/Hydrogenation Products (mole %) |
|---|---|---|---|---|
| 2 | 2-vinyl-5-methyl-1,3-dioxane 15.4 g, 0.12 mole | 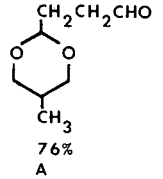 76% A | 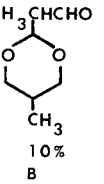 10% B | 1,4-butanediol (70.2) 2-methyl-1,3-propanediol (71.6) |
| 3 | 2-vinyl-5,5-dimethyl-1,3-dioxane 17.1 g, 0.12 mole | 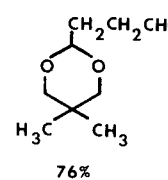 76% A | 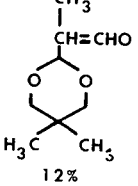 12% B | 1,4-butanediol (73.5) 2-methyl-1,3-propanediol (6.5) 2,2-dimethyl-1,3-propanediol (80.0) |
| 4 | 2-vinyl-4,4,6-trimethyl-1,3-dioxane 18.8 g, 0.12 mole | 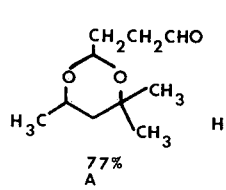 77% A | 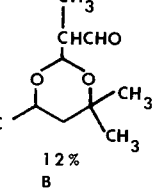 12% B | 1,4-butanediol (74.4) 2-methyl-1,3-propanediol (6.2) 2-methyl-2,4-pentanediol (80.6) |
| 5 | 2-vinyl-4-methyl-1,3-dioxane 15.4 g, 0.12 mole | 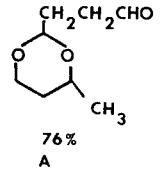 76% A | 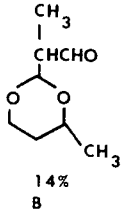 14% B | 1,4-butanediol (71.9) 2-methyl-1,3-propanediol (5.8) 1,3-butanediol (77.6) |
| 6 | 2-vinyl-4-methyl-1,3-dioxolane 13.7 g, 0.12 mole | 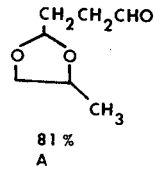 81% A | 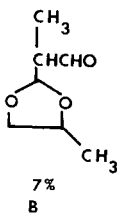 7% B | 1,4-butanediol (74.4) 2-methyl-1,3-propanediol (6.0) 1,2-propanediol (79.0) |

By contrast to the results in Examples 1 and 2, the acetal-aldehydes of Examples 3–6, after being hydrolyzed and hydrogenated, yield more than two diols.

While the invention has been described in considerable detail in the foregoing, it is to be understood that such detail is solely for the purpose of illustration and that variations can be made by those skilled in the art without departing from the spirit and scope of the invention except as set forth in the claims.

What is claimed is:

1. The cyclic acetal-aldehyde mixture of 2(2'-propanal)-5-methyl-1,3-dioxane and 2(3'-propanal)-5-methyl-1,3-dioxane.

* * * * *